(12) United States Patent
Choo et al.

(10) Patent No.: US 8,101,560 B2
(45) Date of Patent: Jan. 24, 2012

(54) LUBRICANT BASE OIL OF PALM ORIGIN

(75) Inventors: Yuen May Choo, Selangor Darul Ehsan (MY); Sit Foon Cheng, Selangor Darul Ehsan (MY); Ah Ngan Ma, Selangor Darul Ehsan (MY); Basiron Yusof, Selangor Darul Ehsan (MY)

(73) Assignee: Malaysian Palm Oil Board, Selangor Darul Ehsan (MY)

( * ) Notice: Subject to any disclaimer, the term of this patent is extended or adjusted under 35 U.S.C. 154(b) by 1049 days.

(21) Appl. No.: 10/979,782

(22) Filed: Nov. 1, 2004

(65) Prior Publication Data

US 2005/0119137 A1 Jun. 2, 2005

(30) Foreign Application Priority Data

Oct. 31, 2003 (MY) .............................. PI 20034185

(51) Int. Cl.
*C10M 105/38* (2006.01)

(52) U.S. Cl. ....................................... 508/485

(58) Field of Classification Search .............. 508/463, 508/468, 472, 473, 485, 494; 554/174
See application file for complete search history.

(56) References Cited

U.S. PATENT DOCUMENTS

| | | | | |
|---|---|---|---|---|
| 2,264,305 A | | 12/1941 | Gibbs | |
| 3,060,210 A | * | 10/1962 | De Groote et al. | 507/244 |
| 3,071,604 A | * | 1/1963 | Mohan et al. | 554/170 |
| 5,773,391 A | * | 6/1998 | Lawate et al. | 508/257 |
| 6,117,827 A | | 9/2000 | Nagaoka et al. | |
| 2002/0137640 A1 | * | 9/2002 | Memita et al. | 508/485 |
| 2004/0014616 A1 | * | 1/2004 | Genuyt et al. | 508/463 |

FOREIGN PATENT DOCUMENTS

| | | |
|---|---|---|
| GB | 2 264 305 | 8/1993 |
| JP | 03285988 A * | 12/1991 |

* cited by examiner

*Primary Examiner* — Ellen McAvoy
*Assistant Examiner* — Taiwo Oladapo
(74) *Attorney, Agent, or Firm* — Muncy, Geissler, Olds & Lowe, PLLC

(57) ABSTRACT

A cost effective and less energy demanding method of producing ester oils or lubricant base oils, particularly fatty monoesters and fatty polyol esters, by esterifying palm fatty acid, which is abundant from the fat splitting process, with a monohydric alcohol or polyhydric alcohol in the presence of an acid catalyst at elevated temperature wherein an azeotroping agent, particularly toluene, is used to facilitate continuous removal by distillation, of water formed as a by-product during the esterification reaction. The esterification reaction is completed within 5 hours and palm fatty esters as produced with the current method exhibit comparable lubricity and biodegradability.

7 Claims, No Drawings

LUBRICANT BASE OIL OF PALM ORIGIN

RELATED APPLICATION

This application claims priority from Malaysian Patent Application No. 20034185, filed Oct. 31, 2003, which is incorporated by reference in its entirety.

FIELD OF THE INVENTION

This invention relates to the production of fatty esters, which are applicable as lubricant base oil. More particularly, it relates to the production of fatty esters, which are applicable as lubricant base oil, using palm fatty acids.

BACKGROUND OF THE INVENTION

There are basically two types of lubricant—oil and grease. Oil has two components: base oil and additives. Grease has three components: base oil, thickener, and additives. Note that oil and grease both share the components of base oil and additives. The difference between an oil and grease is that grease has a thickener. Additives are blended with the base oil to give the oil certain properties such as corrosion resistance or oxidation inhibition. Generally, mineral oil has been employed as base oil in lubricants.

Biodegradable oils are much sought after to replace non-biodegradable mineral oils with increasing awareness of environmental preservations. Two primary classes of biodegradable oils are vegetable oils and synthetics. Vegetable oils offer good biodegradability. Vegetable oils in their natural form lack sufficient oxidative stability. Low oxidative stability means, if untreated, the oil will oxidize rather quickly during use, becoming thick and polymerizing to a plastic-like consistency. Chemical modification of vegetable oils and/or the use of antioxidants can address this problem, but increase the cost. Another negative point to vegetable oils is their high pour point (the temperature at which oil loses fluidity and does not flow). This problem too can be addressed by winterization, addition of chemical additives (pour point suppressants) and/or blending with other fluids possessing lower pour points, but again increase the cost.

Despite their poor oxidative stability, vegetable oils have high viscosity indices, excellent lubricity in extreme pressure, low volatility and good compatibility with additives. Palm oil which originates from *Elaeis guineensis* possesses all the aforementioned advantages of a vegetable oil. In addition to that, palm oil has better oxidative stability compared to other vegetable oils.

GB patent No. 2,264,305 discloses the use of palm oil liquid fraction derivative, known as palm olein as the base oil to provide a satisfactory lubricant for industrial and automotive requirements. Although palm oil has better oxidative stability compared to other vegetable oils, palm olein is still not the preferred choice to be used as base oil for lubricant as an ester additive is still needed to improve its stability and to prevent crystallization during storage.

U.S. Pat. No. 6,117,827 disclosed a biodegradable base oil of satisfactory low temperature fluidity, oxidative stability, lubricity and of low cloud point. The process for manufacturing the biodegradable base oil is characterized in that hardened palm fractionated oil, high oleic sunflower oil and medium chain triglyceride are mixed and subjected simultaneously to an ester interchange reaction in the presence of an enzymatic catalyst, wherein the enzymatic catalyst is a lipase having a specificity to glyceride positions 1 and 3. Multiple raw materials with stringent requirements are needed for the production of the said biodegradable base oil.

Three most common types of synthetic oils are:
1. Poly-alpha-olefins (PAO)
2. Poly-alkylene glycols (PAG)
3. Ester oils A major disadvantage of both PAOs and PAGs is their poor solubility with regard to additives. Because the additives themselves must also be biodegradable, this limits the additives that can be used to formulate effective biodegradable lubricants from PAOs and PAGs.

Ester oils have acquired increasing importance as high quality biodegradable lubricating oils because of its high performance properties and custom design versatility. Ester families commonly used in synthetic lubrication are diesters, polyol esters, monoesters and trimellitates. However, ester oils are normally for high-end usage because of its higher price compared to other synthetic base oils.

U.S. Pat. No. 5,773,391 disclosed a polyol ester suitable for lubricant application. The polyol ester is produced by esterifying an aliphatic or alicyclic polyol containing from 2 to about 10 hydroxyl groups with an aliphatic monocarboxylic acid mixture derived from a high oleic vegetable oil wherein the oleic content is at least 72 percent and the vegetable oil is canola oil, sunflower oil or peanut oil. The esterification reaction is conducted at temperatures in the vicinity of 75° C. to 200° C. for 5 to about 15 or more hours. The condition needed for the esterification reaction is very energy demanding as heating is needed for up to about 15 or more hours.

SUMMARY OF THE INVENTION

The current invention provides a cost effective and less energy demanding method of producing ester oils or lubricant base oils (herein after referred to as fatty esters), particularly fatty monoesters and fatty polyol esters by esterifying palm fatty acid, which is abundant from the fat splitting process, with a monohydric alcohol or polyhydric alcohol in the presence of an acid catalyst at elevated temperature wherein an azeotroping agent, particularly toluene, is used to facilitate continuous removal by distillation, of water formed as a by-product during the esterification reaction. The esterification reaction is completed within 5 hours and palm fatty esters as produced in the current invention exhibit comparable lubricity and biodegradability minus the problem of oxidative stability as occur by using palm olein directly as lubricant base oil.

DESCRIPTION OF THE INVENTION

In order to provide an understanding of a number of terms and phrases used in this specification and claims, the following definitions are provided.

The term palm fatty acid refers to saturated and non-saturated fatty acids derived from palm oil and/or palm kernel oil having 8-18 carbon atoms, particularly but not exclusively caprylic, capric, lauric, myristic, palmitic, stearic, oleic, linoleic, linolenic acids or a mixture thereof.

The term monohydric alcohol refers to those having 4-12 carbon atoms, particularly but not exclusively butanol, ethylhexanol and their isomers.

The term polyhydric alcohol refers to those having 4-8 carbon atoms, particularly but not exclusively neopentyl glycols, trimethylol propane, pentaerythritol, ethylene glycol and diethyl propanediol.

The term Bronstead or Lewis acid catalyst refers to concentrated sulfuric acid, p-toluene sulfonic acid and acidic ion exchange resin.

The term drying agent refers to a substance which is capable of removing water and applicable for esters, particularly anhydrous sodium sulphate.

The term azeotroping agent refers to a compound which is capable of forming an azeotrope mixture with water, particularly toluene.

The term reactant refers to palm fatty acid, monohydric alcohol, polyhydric alcohol or a mixture thereof.

The term palm fatty ester refers to fatty monoester or fatty polyol ester obtained from esterification of palm fatty acid.

The term solvent refers to volatile azeotroping agent and excess reactant.

The fatty monoesters of the present invention are prepared by esterification of palm fatty acid with monohydric alcohol wherein the monohydric alcohol is present in molar excess of palm fatty acid (not less than 1 mole of monohydric alcohol per 1 mole of palm fatty acid).

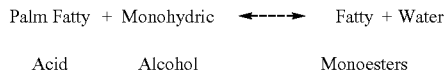

The fatty polyol esters of the present invention are prepared by esterification of palm fatty acid with polyhydric alcohol wherein the palm fatty acid is present in molar excess of polyhydric alcohol (not less than 2 moles of palm fatty acid per 1 mole of polyhydric alcohol).

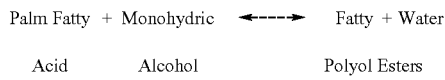

Excess reactant is used to aid the completion of esterification reaction. In the present invention, a molar excess of monohydric alcohol is used in the preparation of fatty monoesters whereas a molar excess of palm fatty acid is used in the preparation of fatty polyol esters. The different choice of excess reactant, besides governed by the stoikiometric equation of the reaction, is mainly influenced by the boiling point of the particular reactant since excess reactant needs to be removed totally after the reaction. Thus, normally the more easily remove reactant would be in excess.

The esterification reaction can be conducted at a relatively moderate temperature and yet achieve high conversion rates over short reaction time by the use of an azeotroping agent to assist the removal of water formed as a by-product of the reaction, thus drive the reaction to completion.

The esterification reaction is effected utilizing a Bronstead or Lewis acid catalyst at temperatures in the vicinity of 80° C. to 210° C., more particularly in the vicinity of 80° C. to 150° C. for production of fatty monoesters and in the vicinity of 120° C. to 210° C. for production of fatty polyol esters. The esterification reaction is complete in not more than 5 hours.

The preferred azeotroping agent is toluene. Addition of aforementioned azeotroping agent helps to facilitate the removal of water from the reaction mixture by distillation. The water is removed in the form of a binary mixture (water and toluene) and/or ternary mixture (water, alcohol and toluene). Addition of toluene helps the removal of water since the boiling point of the azeotrope mixture (85° C.) is lower than the boiling point of water (100° C.). When the azeotrope mixture is condensed at the separating funnel, it separates into two layers wherein the bottom layer is water and the top layer is an organic phase. The bottom layer of water collected at the separating funnel is drained from time to time. At a time during the reaction, the organic phase would overflow and recycle back to the reaction mixture. This is an important aspect as to ensure a substantial amount of toluene is present in the reaction mixture in order to form an azeotrope mixture with water.

Excess solvent is removed from the palm fatty esters produced by means of rotary evaporation and then homogeneous acid catalyst is removed by repeated washing with water. After that, the palm fatty ester produced is dried with a drying agent and underwent further purification to remove excess palm fatty acid, impurities and trace solvent. The step of acid catalyst removal is simplified if heterogeneous acid catalyst is used as it can be removed by simple filtration.

The preferred embodiment of the present invention is as written below:

Production of Fatty Monoesters as Lubricant Base Oil

A stoikiometric mixture of palm fatty acid and monohydric alcohol is transferred into a reaction flask. A molar excess of monohydric alcohol is then added to the reaction mixture. Then, the reaction flask is equipped with a modified Dean and Stark distillation set-up, magnetic stirrer, condenser, dropping funnel and heating plate. An amount of toluene is added to the reaction mixture. Later, a catalytic amount of acid catalyst is added slowly to the reaction mixture when it has reached the temperature in the vicinity of 80° C. to 150° C. Heating continued for not more than 5 hours. Water formed as by-product of the esterification reaction is removed continuously by means of distillation with the aid of toluene while toluene is recycled continuously back to the reaction mixture.

After the reaction is completed, the crude product is cooled to ambient temperature. Then, excess solvent is removed from the crude product by means of rotary evaporation. If homogeneous acid catalyst is utilized in the esterification reaction, it is removed by repeated washing with water until the product produced is neutral. After that, the product is dried with anhydrous sodium sulphate and the hydrated sodium sulphate is later removed from the dried product. The dried product is further purified by using a column packed with silica gel. Trace solvent is further removed by a vacuum pump and finally unreacted palm fatty acid is removed by means of vacuum distillation. Unreacted palm fatty acid would remain as residue while fatty monoester would be collected as distillate. The step of acid catalyst removal is simplified if heterogeneous acid catalyst is used as it can be removed by simple filtration and no washing required.

Production of Polyol Esters as Lubricant Base Oil

A stoikiometric mixture of palm fatty acid and polyhydric alcohol is transferred into a reaction flask. Two molar excess of fatty acid are then added to the reaction mixture. Then, the reaction flask is equipped with a modified Dean and Stark distillation set-up, magnetic stirrer, condenser, dropping funnel and heating plate. An amount of toluene is added to the reaction mixture. Later, a catalytic amount of acid catalyst is added slowly to the reaction mixture when it has reached the temperature in the vicinity of 120° C. to 210° C. Heating continued for not more than 5 hours. Water formed as by-product of the esterification reaction is removed continuously by means of distillation with the aid of toluene while toluene is recycled continuously back to the reaction mixture.

After the reaction is completed, the crude product is cooled to ambient temperature. Then, excess solvent is removed from the crude product by means of rotary evaporation. If homogeneous acid catalyst is utilized in the esterification reaction, it is removed by repeated washing with water until the product produced is neutral. After that, the product is dried with anhydrous sodium sulphate and the hydrated sodium sulphate is later removed from the dried product. The dried product is further purified by using a column packed with silica gel. Trace solvent is further removed by a vacuum pump and finally unreacted palm fatty acid is removed by means of vacuum distillation. Unreacted palm fatty acid would remain as residue while fatty polyol ester would be collected as distillate. The step of acid catalyst removal is simplified if heterogeneous acid catalyst is used as it can be removed by simple filtration and no washing required.

The following examples are presented for the purpose of illustration only, and not intended to be construed in a limiting sense.

Example 1

Production of Butyl Ester as Lubricant Base Oil

A reaction mixture of 1 mole of palm fatty acid and 3 moles of butanol is transferred into a reaction flask. The reaction flask is equipped with a modified Dean and Stark distillation set-up, magnetic stirrer, condenser, dropping funnel and heating plate. 1 mole of toluene is added to the reaction mixture. 1 weight percent of sulphuric acid (based on weight of sulphuric acid/weight of palm fatty acid used) is added to the reaction mixture when it has reached the temperature of 120° C. Heating continued for not more than 5 hours. Water formed as by-product of the esterification reaction is removed continuously by means of distillation with the aid of toluene while toluene is recycled continuously back to the reaction mixture.

After the reaction is completed, the crude product is cooled to ambient temperature. Then, excess solvent is removed from the crude product by means of rotary evaporation. Sulphuric acid is removed by repeated washing with water until the product produced is neutral. After that, the product is dried with anhydrous sodium sulphate and the hydrated sodium sulphate is later removed from the dried product. The dried product is further purified by using a column packed with silica gel. Trace solvent is further removed by a vacuum pump and finally unreacted palm fatty acid is removed by means of vacuum distillation. Unreacted palm fatty acid would remain as residue while butyl ester would be collected as distillate.

Example 2

Production of 2-Ethylhexyl Ester as Lubricant Base Oil 2-ethylhexyl ester is produced by substituting butanol with 2-ethylhexanol in Example 1 and 2-ethylhexyl ester instead of butyl ester is collected as distillate in the final step.

Example 3

Production of Pentaerythritol Ester as Lubricant Base Oil

A reaction mixture of 5 moles of palm fatty acid and 2 moles of pentaerythritol is transferred into a reaction flask. The reaction flask is equipped with a modified Dean and Stark distillation set-up, magnetic stirrer, condenser, dropping funnel and heating plate. 1 mole of toluene is added to the reaction mixture. 1 weight percent of sulphuric acid (based on weight of sulphuric acid/weight of palm fatty acid used) is added to the reaction mixture when it has reached the temperature of 160° C. Heating continued for not more than 5 hours. Water formed as by-product of the esterification reaction is removed continuously by means of distillation with the aid of toluene while toluene is recycled continuously back to the reaction mixture.

After the reaction is completed, the crude product is cooled to ambient temperature. Then, excess solvent is removed from the crude product by means of rotary evaporation. Sulphuric acid is removed by repeated washing with water until the product produced is neutral. After that, the product is dried with anhydrous sodium sulphate and the hydrated sodium sulphate is later-removed from the dried product. The dried product is further purified by using a column packed with silica gel. Trace solvent is further removed by a vacuum pump and finally unreacted palm fatty acid is removed by means of vacuum distillation. Unreacted palm fatty acid would remain as residue while pentaerythritol ester would be collected as distillate.

Example 4

Production of Neopentyl Glycol Ester as Lubricant Base Oil

A reaction mixture of 3 moles of palm fatty acid and 1 mole of neopentyl glycol is transferred into a reaction flask. The reaction flask is equipped with a modified Dean and Stark distillation set-up, magnetic stirrer, condenser, dropping funnel and heating plate. 1 mole of toluene is added to the reaction mixture. 1 weight percent of sulphuric acid (based on weight of sulphuric acid/weight of palm fatty acid used) is added to the reaction mixture when it has reached the temperature of 160° C. Heating continued for not more than 5 hours. Water formed as by-product of the esterification reaction is removed continuously by means of distillation with the aid of toluene while toluene is recycled continuously back to the reaction mixture.

After the reaction is completed, the crude product is cooled to ambient temperature. Then, excess solvent is removed from the crude product by means of rotary evaporation. Sulphuric acid is removed by repeated washing with water until the product produced is neutral. After that, the product is dried with anhydrous sodium sulphate and the hydrated sodium sulphate is later removed from the dried product. The dried product is further purified by using a column packed with silica gel. Trace solvent is further removed by a vacuum pump and finally unreacted palm fatty acid is removed by means of vacuum distillation. Unreacted palm fatty acid would remain as residue while neopentyl glycol ester would be collected as distillate.

Example 5

Production of Trimethylol Propane Ester as Lubricant Base Oil

A reaction mixture of 4 moles of palm fatty acid and 1 mole of trimethylol propane is transferred into a reaction flask. The reaction flask is equipped with a modified Dean and Stark distillation set-up, magnetic stirrer, condenser, dropping funnel and heating plate. 1 mole of toluene is added to the reaction mixture. 1 weight percent of sulphuric acid (based on weight of sulphuric acid/weight of palm fatty acid used) is added to the reaction mixture when it has reached the temperature of 160° C. Heating continued for not more than 5 hours. Water formed as by-product of the esterification reaction is removed continuously by means of distillation with the aid of toluene while toluene is recycled continuously back to the reaction mixture.

After the reaction is completed, the crude product is cooled to ambient temperature. Then, excess solvent is removed from the crude product by means of rotary evaporation. Sulphuric acid is removed by repeated washing with water until the product produced is neutral. After that, the product is dried with anhydrous sodium sulphate and the hydrated sodium sulphate is later removed from the dried product. The dried product is further purified by using a column packed with silica gel. Trace solvent is further removed by a vacuum pump and finally unreacted palm fatty acid is removed by means of vacuum distillation. Unreacted palm fatty acid would remain as residue while trimethylol propane ester would be collected as distillate.

Example 6

Production of n-Butyl Palmitate as Lubricant Base Oil

A reaction mixture of 1 mole of palmitate acid and 3 moles of n-butanol is transferred into a reaction flask. The reaction flask is equipped with a modified Dean and Stark distillation set-up, magnetic stirrer, condenser, dropping funnel and heating plate. 1 mole of toluene is added to the reaction mixture. 40 weight percent of acidic ion exchange resin (based on weight of acidic ion exchange resin/weight of palm fatty acid used) is added to the reaction mixture when it has reached the temperature 120° C. Concentration of active sites for the acidic ion exchange resins used is not less than 1.7 equivalents per litre or not less than 4.7 equivalents per kilogram. Heating continued for not more than 5 hours. Water formed as by-product of the esterification reaction is removed continuously by means of distillation with the aid of toluene while toluene is recycled continuously back to the reaction mixture.

After the reaction is completed, the crude product is cooled to ambient temperature. Then, excess solvent is removed from the crude product by means of rotary evaporation. The product is dried with anhydrous sodium sulphate and the hydrated sodium sulphate is later removed from the dried product along with acidic ion exchange resin. The dried product is further purified by using a column packed with silica gel. Trace solvent is further removed by a vacuum pump and finally unreacted palmitate acid is removed by means of vacuum distillation. Unreacted palmitate acid would remain as residue while n-butyl ester would be collected as distillate.

Example 7

Viscosity at 40° C. and 100° C. for palm fatty esters as produced by using method of the present invention are shown below. The viscosities are determined according to ASTM D445.

TABLE 1

Viscosity at 40° C. and 100° C. for Fatty Monoesters

| Fatty Monoester | Viscosity (cSt) | |
| --- | --- | --- |
| | 40° C. | 100° C. |
| n-Butyl Palmitate | 5.58 | 2.04 |
| n-Butyl Oleate | 6.00 | 2.17 |
| n-Butyl Stearate | 7.17 | 2.45 |
| 2-Butyl Palmitate | 5.73 | 2.09 |

TABLE 1-continued

Viscosity at 40° C. and 100° C. for Fatty Monoesters

| Fatty Monoester | Viscosity (cSt) | |
| --- | --- | --- |
| | 40° C. | 100° C. |
| 2-Butyl Oleate | 6.56 | 2.22 |
| 2-Butyl Stearate | 7.34 | 2.48 |
| 2-Ethylhexyl Palmitate | 7.98 | 2.53 |
| 2-Ethylhexyl Stearate | 7.71 | 2.22 |
| n-Butyl Palmitate & n-Butyl Stearate | 6.39 | 2.23 |
| n-Octyl Oleate | 9.11 | 2.87 |
| Oleyl Caprylate | 10.34 | 3.16 |

TABLE 2

Viscosity at 40° C. and 100° C. for Fatty Polyol Esters

| Fatty Polyol Ester | Viscosity (cSt) | |
| --- | --- | --- |
| | 40° C. | 100° C. |
| Neopentylglycol Dicaprylate | 7.18 | 2.34 |
| Neopentylglycol Dicaprate | 10.20 | 2.73 |
| Neopentylglycol Dilaurate | 15.58 | 4.21 |
| Neopentylglycol Dioleate | 26.90 | 6.69 |
| Pentaerythritol Tetracaprylate | 21.84 | 4.41 |
| Pentaerythritol Tetracaprate | 23.49 | 4.33 |
| Trimethylolpropane Tricaprylate | 20.96 | 4.96 |
| Trimethylolpropane Tricaprate | 22.45 | 4.14 |
| TrimethylolpropaneTrioleate | 40.95 | 8.85 |
| Diethyleneglycol Dioleate | 21.45 | 5.50 |
| Diethylpropanedioyl Dioleate | 31.47 | 6.88 |
| Ethyleneglycol Dioleate | 18.62 | 4.99 |

Example 8

Viscosity index for palm fatty esters as produced by using method of the present invention is shown below. The viscosity indices are determined according to ASTM D2270.

TABLE 3

Viscosity Index for Fatty Monoesters

| Fatty Monoester | Viscosity Index |
| --- | --- |
| n-Butyl Palmitate | 196 |
| n-Butyl Oleate | 207 |
| n-Butyl Stearate | 199 |
| 2-Butyl Palmitate | 203 |
| 2-Butyl Oleate | 186 |
| 2-Butyl Stearate | 167 |
| 2-Ethylhexyl Palmitate | 161 |
| 2-Ethylhexyl Stearate | 190 |
| n-Octyl Oleate | 185 |
| Oleyl Caprylate | 189 |

TABLE 4

Viscosity Index for Fatty Polyol Esters

| Fatty Polyol Ester | Viscosity Index |
| --- | --- |
| Neopentylglycol Dicaprylate | 119 |
| Neopentylglycol Dicaprate | 140 |
| Neopentylglycol Dilaurate | 147 |
| Neopentylglycol Dioleate | 210 |
| Pentaerythritol Tetracaprylate | 123 |
| Pentaerythritol Tetracaprate | 156 |
| Trimethylolpropane Tricaprylate | 156 |
| Trimethylolpropane Tricaprate | 187 |

TABLE 4-continued

Viscosity Index for Fatty Polyol Esters

| Fatty Polyol Ester | Viscosity Index |
| --- | --- |
| TrimethylolpropaneTrioleate | 190 |
| Diethyleneglycol Dioleate | 214 |
| Diethylpropanedioyl Dioleate | 188 |
| Ethyleneglycol Dioleate | 216 |

Example 9

Flash point for palm fatty esters as produced by using method of the present invention is shown below. The flash points are determined according to ASTM D93.

TABLE 5

Flash Point for Fatty Monoesters

| Fatty Monoester | Flash Point (° C.) |
| --- | --- |
| n-Butyl Palmitate | 160 |
| n-Butyl Oleate | 210 |
| n-Butyl Stearate | 218 |
| 2-Butyl Palmitate | 186 |
| 2-Butyl Oleate | 176 |
| 2-Butyl Stearate | 198 |
| 2-Ethylhexyl Palmitate | 140 |
| 2-Ethylhexyl Stearate | 120 |
| n-Butyl Palmitate & n-Butyl Stearate | 202 |
| n-Octyl Oleate | 178 |
| Oleyl Caprylate | 190 |

TABLE 6

Flash Point for Fatty Polyol Esters

| Fatty Polyol Ester | Flash Point (° C.) |
| --- | --- |
| Neopentylglycol Dicaprylate | 195 |
| Neopentylglycol Dicaprate | 175 |
| Neopentylglycol Dilaurate | 178 |
| Neopentylglycol Dioleate | 230 |
| Pentaerythritol Tetracaprylate | 160 |
| Pentaerythritol Tetracaprate | 150 |
| Trimethylolpropane Tricaprylate | 168 |
| Trimethylolpropane Tricaprate | 184 |
| TrimethylolpropaneTrioleate | 124 |
| Diethyleneglycol Dioleate | 170 |
| Diethylpropanedioyl Dioleate | 240 |
| Ethyleneglycol Dioleate | 140 |

Example 10

Water separability at 54° C. for palm fatty esters as produced by using method of the present invention is shown below. The water separabilities are determined according to ASTM D892.

TABLE 7

Water Separability for Fatty Monoesters

| Fatty Monoester | Water Separability (minutes) |
| --- | --- |
| n-Butyl Palmitate | 5 |
| n-Butyl Oleate | 5 |
| n-Butyl Stearate | 5 |
| 2-Butyl Palmitate | 30 |
| 2-Butyl Oleate | 5 |

TABLE 7-continued

Water Separability for Fatty Monoesters

| Fatty Monoester | Water Separability (minutes) |
| --- | --- |
| 2-Butyl Stearate | 5 |
| 2-Ethylhexyl Palmitate | 25 |
| 2-Ethylhexyl Stearate | 5 |
| n-Butyl Palmitate & n-Butyl Stearate | 5 |
| n-Octyl Oleate | 3 |
| Oleyl Caprylate | 6 |

TABLE 8

Water Separability for Fatty Polyol Esters

| Fatty Polyol Ester | Water Separability (minutes) |
| --- | --- |
| Neopentylglycol Dicaprylate | 13 |
| Neopentylglycol Dicaprate | 17 |
| Neopentylglycol Dilaurate | 27 |
| Neopentylglycol Dioleate | 10 |
| Pentaerythritol Tetracaprylate | 21 |
| Pentaerythritol Tetracaprate | 18 |
| Trimethylolpropane Tricaprylate | 27 |
| Trimethylolpropane Tricaprate | 10 |
| TrimethylolpropaneTrioleate | 20 |
| Diethyleneglycol Dioleate | 8 |
| Diethylpropanedioyl Dioleate | 8 |
| Ethyleneglycol Dioleate | 11 |

Example 11

Moisture content for palm fatty esters as produced by using method of the present invention is shown below. The moisture contents are determined according to ASTM E1064.

TABLE 9

Moisture Content for Fatty Monoesters

| Fatty Monoester | Moisture Content (ppm) |
| --- | --- |
| n-Butyl Palmitate | 195 |
| n-Butyl Oleate | 530 |
| n-Butyl Stearate | 442 |
| 2-Butyl Palmitate | 54 |
| 2-Butyl Oleate | 94 |
| 2-Butyl Stearate | 167 |
| 2-Ethylhexyl Palmitate | 81 |
| 2-Ethylhexyl Stearate | 711 |
| n-Butyl Palmitate & n-Butyl Stearate | 517 |
| n-Octyl Oleate | 129 |
| Oleyl Caprylate | 72 |

TABLE 10

Moisture Content for Fatty Polyol Esters

| Fatty Polyol Ester | Moisture Content (ppm) |
| --- | --- |
| Neopentylglycol Dicaprylate | 140 |
| Neopentylglycol Dicaprate | 112 |
| Neopentylglycol Dilaurate | 98 |
| Neopentylglycol Dioleate | 64 |
| Pentaerythritol Tetracaprylate | 89 |
| Pentaerythritol Tetracaprate | 87 |
| Trimethylolpropane Tricaprylate | 98 |
| Trimethylolpropane Tricaprate | 154 |
| TrimethylolpropaneTrioleate | 105 |
| Diethyleneglycol Dioleate | 55 |
| Diethylpropanedioyl Dioleate | 47 |
| Ethyleneglycol Dioleate | 106 |

What is claimed is:

1. A process of producing lubricant base oil consisting of the steps of
   a) esterifying oleic acid with a polyhydric alcohol selected from diethyl propanediol in the presence of an acid catalyst selected from sulfuric acid, p-toluene sulfonic acid and acidic ion exchange resin at elevated temperature to yield diethylpropanedioyl dioleate,
   b) continuously removing water formed as a by-product during the reaction in (a) by distillation,
   c) removing the acid catalyst, impurities, and solvent from the resultant product of step (a) and (b), and
   d) in step (b) adding an azeotroping agent to facilitate continuous removal of water to yield a lubricant base oil, wherein the moisture content of the lubricant base oil is not more than 600 ppm, and the water separability of the lubricant base oil is not more than 30 minutes.

2. The process of claim 1 wherein the azeotroping agent is toluene.

3. The process of claim 1 wherein the elevated temperature is in the vicinity of 80° C. to 210° C.

4. The process of claim 1 wherein the elevated temperature is in the vicinity of 120° C. to 210° C.

5. The process of claim 1 wherein the concentrated sulphuric acid or p-toluene sulphonic acid is present in an amount of 0.5 to 1.0 weight percent based on weight of the acid mentioned per weight of the palm fatty acid used.

6. The process of claim 1 wherein the acidic ion-exchange resin is present in an amount of 40 weight percent based on weight of the resin mentioned per weight of the palm fatty acid used.

7. A process of producing lubricant base oil consisting of the steps of
   (i) esterifying oleic acid with a polyhydric alcohol selected from diethyl propanediol in the presence of an acid catalyst selected from sulfuric acid, p-toluene sulfonic acid and acidic ion exchange resin at a temperature in the vicinity of 120° C. to 210° C. for less than 5 hours wherein not less than 2 moles of palm fatty acid are present per mole of polyhydric alcohol used to yield diethylpropanedioyl dioleate,
   (ii) using toluene to facilitate continuous removal by distillation, of water formed as a by-product during the esterification reaction,
   (iii) purifying the product obtained from (ii) by removing acid catalyst, solvent, and impurities to yield a lubricant base oil, wherein the moisture content of the lubricant base oil is not more than 600 ppm, and the water separability of the lubricant base oil is not more than 30 minutes.

* * * * *